(12) United States Patent
Kataoka et al.

(10) Patent No.: US 8,048,855 B1
(45) Date of Patent: Nov. 1, 2011

(54) METHOD FOR SUPPRESSING GRAFT-VERSUS-HOST-DISEASE

(75) Inventors: Motoyuki Kataoka, Tokyo (JP); Kaname Yamamoto, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 763 days.

(21) Appl. No.: 10/111,097

(22) PCT Filed: Oct. 20, 2000

(86) PCT No.: PCT/JP00/07320
§ 371 (c)(1), (2), (4) Date: Aug. 21, 2002

(87) PCT Pub. No.: WO01/28581
PCT Pub. Date: Apr. 26, 2001

(30) Foreign Application Priority Data

Oct. 20, 1999 (JP) .................................... 11-298027

(51) Int. Cl.
*A61K 38/18* (2006.01)
*C12N 5/07* (2010.01)

(52) U.S. Cl. .......................... 514/7.6; 435/335; 435/343

(58) Field of Classification Search .................. 514/1, 2; 536/23.5; 530/350, 351, 399, 402, 300; 435/325, 435/7.1
See application file for complete search history.

(56) References Cited

U.S. PATENT DOCUMENTS

| | | | | |
|---|---|---|---|---|
| 5,800,539 | A | * | 9/1998 | Waller .......................... 424/577 |
| 5,806,529 | A | * | 9/1998 | Reisner et al. ................. 128/898 |
| 5,880,090 | A | * | 3/1999 | Hammond et al. ............... 514/2 |
| 6,162,427 | A | * | 12/2000 | Baumann et al. ............ 424/85.1 |

OTHER PUBLICATIONS

Martin et al. Haematologica, 1996 81:464-467.*
Kokai et al. Artificial Organs, 1996 20(8):883-889.*
Iizuka et al. Blood, 1997 89(4):1446-1451.*
Bishop et al., A randomized, double-blind trial of filgrastim (granulocyte colony-stimulating factor) versus placebo following allogeneic blood stem cell transplantation, Jul. 2000, vol. 96, Issue 1, pp. 80-85.*
Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-132.*
Doerks et al., Protein annotation: detective work for function prediction, 1998, Trends in Genetics, vol. 14, pp. 248-250.*
Ngo et al., The protein folding problem and tertiary structure prediction,1994, pp. 492-495.*
Skolnick et al., From genes to protein structure and function: novel applications of computational approaches in the genomic era, 2000, Trends in Biotech, vol. 18, Issue 1, pp. 34-39.*
Smith et al., The challenge of genome sequence annotation or "the devil is in the details", 1997, Nature Biotechnology, vol. 15, pp. 1222-1223.*
Wells et al., Addivity of mutational effects in proteins, 1990, Biochemistry, vol. 29, pp. 8509-8517.*
M. Hirokawa et al., "Modulation of Allogeneic Immune Responses by Filgrastim (Recombinant Human Granulocyte Colony-Stimulating Factor) In Bone Marrow Transplantation", *Chemical Abstracts*, vol. 124, No. 17, abstract No. 221547q, (1996).
O. Ringden et al., "Peripheral Blood Stem Cell Transplantation From Unrelated Donors: A Comparison With Marrow Transplantation", *Blood*, vol. 94, No. 2, pp. 455-464 (Jul. 15, 1999).
A. M. Marmont et al., "T-Cell Depletion of HLA-Identical Transplants in Leukemia", *Blood*, vol. 78, No. 8, pp. 2120-2130 (Oct. 15, 1991).
M. Hirokawa et al., "Modulation of Allogeneic Immune Responses by Filgrastim (Recombinant Human Granulocyte Colony-Stimulating Factor) In Bone Marrow Transplantation", *International Journal of Hematology*, vol. 62, pp. 235-241 (1995).
M.J. Pittet et al., "Cutting Edge: Cytolytic Effector Function in Human Circulating $CD8^+T$ Cells Closely Correlates with CD56 Surface Expression", *The Journal of Immunology*, pp. 1148-1152 (2000).
S.E. Theocharis et al., "Effect of Two Forms of Granulocyte-Colony-Stimulating Factor on Hepatic Regeneration After 70% Partial Hepatectomy in Rats", *Clinical Science*, vol. 92, pp. 315-320 (1997).
M. Mielcarek et al., "Suppression of Alloantigen-Induced T-Cell Proliferation by $CD14^+$Cells Derived from Granulocyte Colony-Stimulating Factor—Mobilized Peripheral Blood Mononuclear Cells", *Blood*, vol. 89, No. 5, pp. 1629-1634 (Mar. 1, 1997).
C.R. Kusnierz-Glaz et al., "Granulocyte Colony-Stimulating Factor-Induced Comobilization of $CD4^{31}CD8^-$T Cells and Hematopoietic Progenitor Cells ($CD34^+$) in the Blood of Normal Donors", *Blood*, vol. 89, No. 7, pp. 2586-2595 (Apr. 1, 1997).
D. Zeng et al., "Granulocyte Colony-Stimulating Factor Reduces the Capacity of Blood Mononuclear Cells to Induce Graft-Versus-Host Disease: Impact on Blood Progenitor Cell Transplantation", *Blood*, vol. 90, No. 1, pp. 453-463 (Jul. 1, 1997).
B.M. Snadmaier et al., "Allogeneic Transplants of Canine Peripheral Blood Stem Cells Mobilized by Recombinant Canine Hematopoietic Growth Factor", *Blood*, vol. 87, No. 8, pp. 3508-3513 (Apr. 15, 1996).
T. Pollmächer et al., "Effects of granulocyte Colony-Stimulating Factor on Plasma Cytokine and Cytokine Receptor Levels and on the In Vivo Host Response to Endotoxin in Healthy Men", *Blood*, vol. 87, No. 3., pp. 900-905 (Feb. 1, 1996).
L. Pan et al., "Pretreatment of Donor Mice With Granulocyte Colony-Stimulating Factor Polarizes Donor T Lymphocytes Toward Type-2 Cytokine Production and Reduces Severity of Experimental Graft-Versus-Host Disease", *Blood*, vol. 86, No. 12, pp. 4422-4429 (Dec. 15, 1995).

(Continued)

*Primary Examiner* — Robert Landsman
*Assistant Examiner* — Ian Dang

(57) ABSTRACT

A method for effectively suppressing GVHD, which occurs after peripheral blood stem cells allotransplantation, without causing marked side effects, and a pharmaceutical composition intended for this purpose and containing human G-CSF as an active ingredient. GVHD can be suppressed by administering human G-CSF to a transplantation recipient after peripheral blood stem cells transplantation.

1 Claim, 2 Drawing Sheets

OTHER PUBLICATIONS

T. Hartung et al., "Effect of Granulocyte Colony-Stimulating Factor Treatment on Ex Vivo Blood Cytokine Response in Human Volunteers", *Blood*, vol. 85, No. 9, pp. 2482-2489 (May 1, 1995).

J. Tanaka et al., "The Role of Accessory Cells in Allogeneic Peripheral Blood Stem Cell Transplantation", *International Journal of Hematology*, vol. 69, pp. 70-74 (1999).

P.F. Foster et al., "The Use of Granulocyte Colony-Stimulating Factor After Liver Transplantation", *Transplantation*, vol. 59, No. 11, pp. 1557-1563 (Jun. 15, 1995).

R.A. Mann et al., "$CD8^+$, Radiosensitive T Cells of Parental Origin, Oppose Cells Capable of Down-Regulating Cytotoxicity in Murine Acute Lethal Graft-Versus-Host Disease", *Clinical Immunology and Immunopathology*, vol. 89, No. 3, pp. 260-270 (Dec. 1998).

R.D. Allen et al., "Genetics of Graft-Versus-Host Disease, I. A Locus on Chromosome 1 Influences Development of Acute Graft-Versus-Host Disease in a Major Histocompatibility Complex Mismatched Murine Model", *Immunology*, vol. 96, pp. 254-261 (1999).

S. Quaranta et al., "Autoantibodies in Human Chronic Graft-Versus-Host Disease After Hematopoietic Cell Transplantation", *Clinical Immunology*, vol. 91, No. 1, pp. 101-116 (Apr. 1999).

G.R. Brown et al., "Tumor Necrosis Factor Inhibitor Ameliorates Murine Intestinal graft-Versus-Host Disease", *Gastroenterology*, vol. 116, No. 3, pp. 593-601 (1999).

K. Saigo et al., "Therapeutic Strategy for Post-Transfusion Graft-Vs.-Host Disease", *International Journal of Hematology*, pp. 147-151 (1998).

O. Ringden et al., "Increased Risk of Chronic Graft-Versus-Host Disease, Obstructive Bronchiolitis, and Alopecia With Busulfan Versus Total Body Irradiation: Long-Term Results of a Randomized Trial in Allogeneic Marrow Recipients With Leukemia", *Blood*, vol. 93, No. 7, pp. 2196-2201 (Apr. 1, 1999).

R.J. Jones et al., "Induction of Graft-Versus-Host Disease After Autologous Bone Marrow Transplantation", *Blood*, vol. 89, No. 6, pp. 754-756 (1997).

A. D. Hess et al., "Specificity of Effector T Lymphocytes in Autologous Graft-Versus-Host Disease: Role of the Major Histocompatibility Complex Class II Invariant Chain Peptide", *Blood*, vol. 89, No. 6, pp. 2203-2209 (Mar. 15, 1997).

J.L.M. Ferrara et al., "Graft-Versus-Host Disease", *The New England Journal of Medicine*, vol. 324, No. 10, pp. 667-674 (1991).

G. Eberl et al., "Tissue-Specific Segregation of CD1d-Dependent and CD1d-Independent NK T Cells", *The Journal of Immunology*, pp. 6410-6419 (1999).

M.R. Bishop et al., "A Randomized, Double-Blind Trial of Filgrastim (Granulocyte Colony-Stimulating Factor) Versus Placebo Following Allogeneic Blood Stem Cell Transplantation", *Blood*, vol. 96, No. 1, pp. 80-85 (Jul. 1, 2000).

J. Contreras et al., "Mobilized Recipient $CD34^+$Cells Promote Acceptance of Incompatible Primate Allografts Without Immunosuppression", *American Society of Transplantation, AST Eighteenth Annual Mtg.*, (1999).

K. Iizuka et al., "Host F1 Mice Pretreated With Granulocyte Colony-Stimulating Factor Accept Parental Bone Marrow Grafts In Hybrid Resistance System", *Blood*, vol. 89, No. 4, pp. 1446-1451 (Feb. 15, 1997).

K.J.L. Hammond et al., "NKT Cells are Phenotypically and Functionally Diverse", *Eur. J. Immunol.*, vol. 29, pp. 3768-3781 (1999).

H. Nishimura et al., "MHC Class II-Dependent $NK1.1^+v\delta T$ Cells are Induced in Mice by *Salmonella* Infection", *The Journal of Immunology*, pp. 1573-1581 (1999).

G.C. Koo et al., "The NKH-1.1(-) Mouse: A Model To Study Differentiation Of Murine NK Cells", *The Journal of Immunology*, vol. 137, No. 2, pp. 3742-3747 (1986).

M.K. Slifka et al., "NK Markers Are Expressed on A High Percentage Of Virus-Specific $CD8^+$and $CD4^+$T Cells", *The Journal of Immunology*, pp. 2009-2015 (2000).

Y. Kaneko et al., "Augmentation of $V\alpha14$ NKT Cell-Mediated Cytotoxicity by Interleukin 4 in an Autocrine Mechanism Resulting in the Development of Concanavalin A-induced Hepatitis", *J. Exp. Med.*, vol. 191, No. 1, pp. 105-114 (2000).

J. Baker et al., "Expansion of Cytolytic $CD8^+$Natural Killer T Cells With Limited Capacity For Graft-Versus-Host Disease Induction Due to Interferon v Production", *Blood*, vol. 97, No. 10, pp. 2923-2931 (May 15, 2001).

L. Pan et al., "Pretreatment of Donor Mice With Granulocyte Colony-Stimulating Factor Polarizes Donor T Lymphocytes Toward Type-2 Cytokine Production and Reduces Severity of Experimental Graft-Versus-Host Disease", *Blood*, vol. 86, No. 12, pp. 4422-4429 (Dec. 15, 1995).

D. Zeng et al., "Granulocyte Colony-Stimulating Factor Reduces The Capacity Of Blood Mononuclear Cells to Induce Graft-Versus-Host Disease: Impact On Blood Progenitor Cell Transplantation", *Blood*, vol. 90, No. 1, pp. 453-463 (Jul. 1, 1997).

V. Legendre et al., "Selection of Phenotypically Distinct $NK1.1^+T$ Cells Upon Antigen Expression In the Thymus or In the Liver", *Eur. J. Immunol.*, vol. 29, pp. 2330-2343 (1999).

D. Zeng et al., "Heterogeneity of $NK1.1^+T$ Cells in the Bone Marrow: Divergence from the Thymus", *The Journal of Immunology*, pp. 5338-5345 (1999).

K.J.L. Hammond et al., "NKT Cells are Phenotypically and Functionally Diverse", *Eur. J. Immunol.*, vol. 29, pp. 3768-3781 (1999).

K. Sato et al., "Evidence for Extrathymic Generation of Intermediate T Cell Receptor Cells in the Liver Revealed in Thymectomized, Irradiated Mice Subjected to Bone Marrow Transplantation", *J. Exp. Med.*, vol. 182, pp. 759-767 (1995).

L. Pan et al., "Granulocyte Colony-Stimulating Factor-Mobilized Allogeneic Stem Cell Transplantation Maintains Graft-Versus-Leukemia Effects Through a Perforin-Dependent Pathway While Preventing Graft-Versus-Host Disease", *Blood*, vol. 93, No. 12, pp. 4071-4078 (1999).

T. Kambayashi et al., "Emergence of $CD8^+T$ Cells Expressing NK Cell Receptors in Influenza A Virus-Infected Mice", *The Journal of Immunology*, pp. 4964-4969 (2000).

Brice P et al "Hematologic recovery and survival of lymphoma patients after autologous stem-cell transplantation: comparison of bone marrow and peripheral blood progenitor cells" Leukemia & Lymphoma (Aug. 1996) vol. 22, No. 5-6 pp. 449-456.

Masahiro Imamura, M. D.; Junji Tanaka, M.D.; "Hematology & Oncology" vol. 37(5); p. 425-432, 1998.

Foster et al; "The Use of Granulocyte Colony-Stimulating Factor After Liver Transplantation"; *Transplantation*; vol. 59, No. 11, pp. 1557-1583, Jun. 15, 1995.

Nawa et al; "Responses of Granulocyte-Stimulating Factor-Mobilized Peripheral Blood Mononuclear Cells to Alloantigen Stimulation"; *Blood*, vol. 90, No. 4, pp. 1716-1718, 1997.

Murphy et al; "Differential Effects of the Absence of Interferon-γ and IL-4 in Acute Graft-Versus-Host Disease after Allogeneic Bone Marrow Transplantation in Mice"; *The Journal of Clinical Investigation*, vol. 102, No. 9, pp. 1742-7148, Nov. 1998.

Pavletic, Z.S. et al, "Hematopoietic Recovery After Allogeneic Blood Stem-Cell Transplantation Compared with Bone Marrow Transplantation in Patients With Hematologic Malignancies", Journal of Clinical Oncology, vol. 15, No. 4, 1997, pp. 1608-1616, XP000675198.

Kogler, G. et al, "Simultaneous Cord Blood Transplantation of Ex Vivo Expanded Together with Non-expanded Cells for High Risk Leukemia", Database Embase Elsevier Science Publishers, Amsterdam, NL; Database Accession No. EMB-1999300461, XP-001167132 (Abstract), 1999.

Kogler, G. et al, "Simultaneous Cord Blood Transplantation of Ex Vivo Expanded Together with Non-expanded Cells for High Risk Leukemia", Bone Marrow Transplantation, vol. 24, pp. 397-403 (1999) (corresponds to Database Embase Elsevier Science Publishers, Amsterdam, NL; Database Accession No. EMB-1999300461, XP-001167132 submitted with an IDS filed on Oct. 29, 2008).

Bensinger, W.I., "Transplantation of Allogeneic Peripheral Blood Stem Cells Mobilized by Recombinant Human Granulocyte Colony-Stimulating Factor", Blood, vol. 85, No. 6, pp. 1655-1658, (1995).

\* cited by examiner

METHOD FOR SUPPRESSING GRAFT-VERSUS-HOST-DISEASE

TECHNICAL FIELD

This invention relates to a therapeutic agent for graft-versus-host disease (hereinafter referred to as GVHD), which contains human granulocyte-colony stimulating factor (hereinafter referred to as G-CSF) as an active ingredient. More particularly, the invention relates to a pharmaceutical composition containing, as an active ingredient, G-CSF which is effective for treatment of GVHD occurring after peripheral blood stem cell transplantation.

BACKGROUND ART

In recent years, hematopoietic stem cell transplantation has been widely performed for the purpose of treating hematopoietic organ tumor, solid carcinoma, leukemia, or hypoplastic anemia. Hematopoietic stem cell transplantation is classified, according to differences in stem cell sources or a donor's selection, into bone marrow allotransplantation, peripheral blood stem cell transplantation, and cord blood stem cell transplantation between blood relatives or non-blood relatives, and bone marrow autotransplantation, peripheral blood stem cell transplantation, and cord blood stem cell transplantation performed in the donor of the transplanted cells. Of these hematopoietic stem cell transplantation techniques, bone marrow allotransplantation is a widespread method of treatment, but poses the problem of a heavy burden on the donor associated with bone marrow collection.

Recently, the clinical application of peripheral blood stem cell allotransplantation has proceeded in place of bone marrow allotransplantation imposing a heavy burden on the donor. Peripheral blood stem cell allotransplantation has advantages, such as a light burden on the donor during hematopoietic stem cell harvest, and prompt recovery of the recipient's neutrophils and thrombocytes. However, peripheral blood stem cell transplantation causes GVHD as does bone marrow transplantation, and its control has become a problem.

GVHD is a generic name for diseases due to an immune reaction which immunocompetent cells transferred or transplanted into a host causes against the tissues of the host. A major cause of GVHD is believed to be the immune response of immunocompetent cells, such as mature T cells contained in the peripheral blood transferred or transplanted, against the recipient's tissues. GVHD includes acute and chronic diseases, with clinical manifestations ranging from dermal symptoms to diarrhea and jaundice, and shows severe, sometimes lethal, response.

Methods for suppressing GVHD have been by the use of immunosuppressants such as methotrexate and cyclosporin A, and the removal of mature T cells from a transplanted cell population (graft). When methotrexate or cyclosporin A is used, side effects of such drugs on the living organism present a major problem. The side effect of cyclosporin A is strong renal toxicity, and the side effect of methotrexate is bone marrow depression.

GVHD can be suppressed by the removal of mature T cells from the transplanted cell population, but this method has been shown in that suppression of anti-tumor activity, as noticed by relapse of leukemia (see Blood, 78:2120-2123, 1991). Thus, the T cell removal therapy requires a check for ensuring the anti-tumor effect.

Various studies are under way to investigate influence on GVHD in a recipient who underwent transplantation of hematopoietic stem cells induced by the administration of granulocyte-colony stimulating factor (G-CSF) to a donor. It has been reported that when G-CSF is administered to a human, mononuclear cells or $CD4^-CD8^-\alpha\beta^+$ cells increase, and these cells can suppress the proliferation potency of T cells (see Clinical Immunology, 30(6):833-838, 1998). There is also a report that when G-CSF is administered after bone marrow allotransplantation (Allo-BMT), the occurrence of acute GVHD tends to be suppressed in comparison with a group without receiving G-CSF (see Int. J. Hematol., 62:235, 1995). However, a peripheral blood stem cell population for use in transplantation, as compared with a bone marrow cell population, has a markedly low number of stem cells proportion and is also different in the properties of stem cells. Thus, the mechanism of the action of suppressing GVHD occurring after peripheral blood stem cell transplantation has been suspected to differ from that by bone marrow cell transplantation.

In the peripheral blood, the number of hematopoietic stem cells is much smaller than in the bone marrow. Thus, it is common practice to induce peripheral blood stem cells by the administration of G-CSF to the donor. It has been reported that a cell population from the donor in a G-CSF treatment group is advantageous for defense against infection or an anti-tumor activity, but a further careful analysis is desired in connection with induction and aggravation of GVHD. Particularly, the relationship between in vivo administration of G-CSF in the donor and the recipient's chronic GVHD occurring after transplantation of peripheral blood stem cells induced thereby remains insufficiently analyzed (see Hematology & Oncology 37(5):425-432, 1998).

Under these conditions, a demand has been made for the development of a method, which causes few side effects and effectively suppresses GVHD potentially occurring after peripheral blood stem cell Allotransplantation, or a drug used for this purpose.

DISCLOSURE OF THE INVENTION

The present inventors have found that after peripheral blood allotransplantation is performed, GVHD can be suppressed, unexpectedly without noticeable side effects, by administration of G-CSF to the recipient. The present invention has been accomplished based on this finding.

Figure 1:
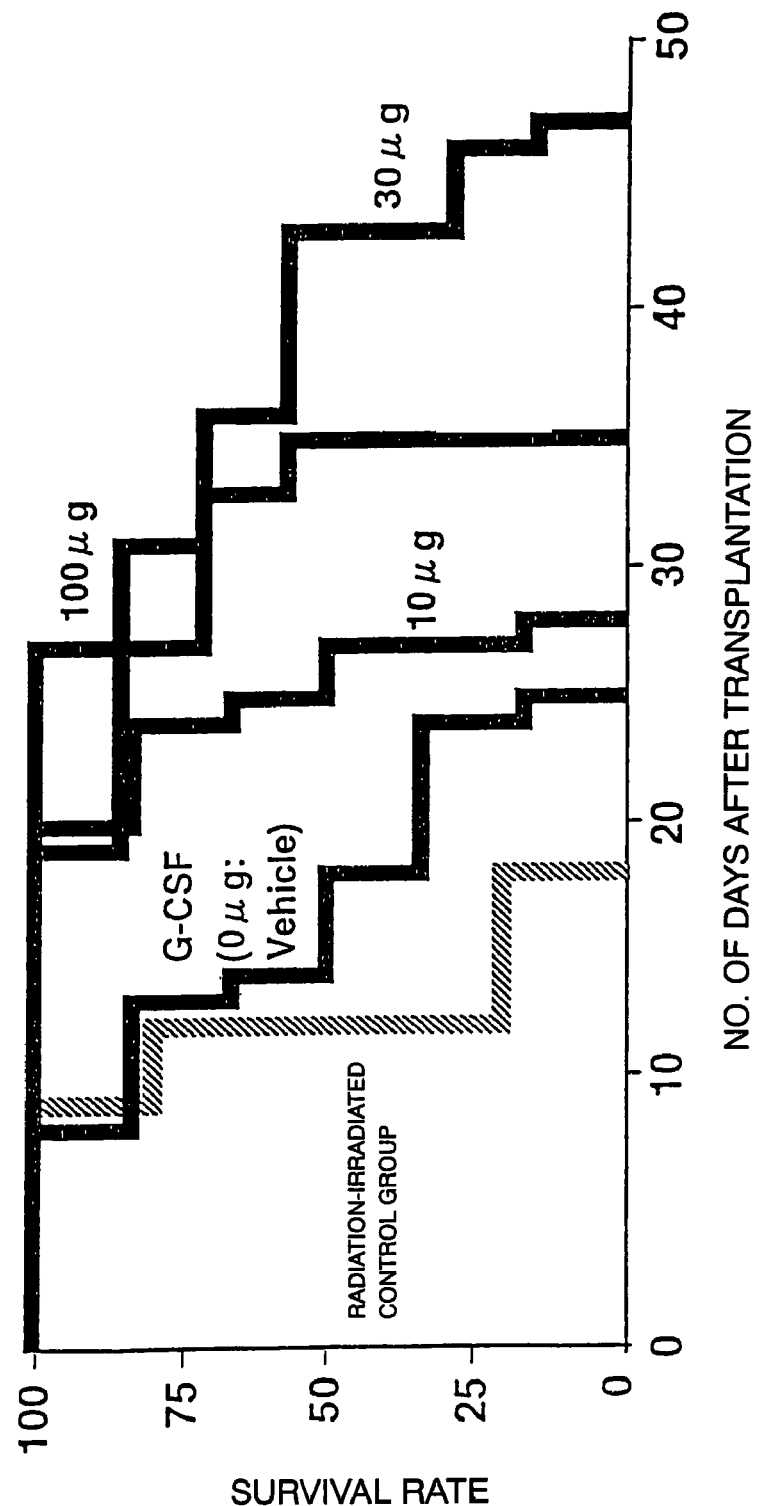
FIG. 1 is a graph showing the effect of G-CSF administration on the survival rate in recipient mice into which splenic cells of donor mice administered G-CSF were transferred through the tail vein.

The present inventors administered G-CSF to donor mice to induce stem cells. They transplanted splenic cells (hereinafter referred to as SPC), including the stem cells, into recipient mice, in which the function of immunocompetent cells had been inactivated by irradiation with X-rays, to cause GVHD. After SPC transplantation, G-CSF was administered to the recipient mice. These mice showed survival-prolongation in comparison with a control group (a group receiving without G-CSF). This phenomenon was considered to result from the suppression of GVHD (see Experimental Example 1).

When the GVHD was judged by the degree of depilation, the recipient mice of the G-CSF treatment group showed a tendency toward improvement as compared with the control group. The recipient mice of the control group developed GVHD after SPC transplantation, and markedly increased in NK1.1$^+$, CD8$^+$ cells in peripheral blood mononuclear cells in comparison with the normal mice. Like NK1.1$^+$, CD8$^+$ cells, CD56$^+$CD8$^+$ cells, express for both of a human NK marker and a CD8 T cell marker, show a cytotoxic activity (J. Immunol. (2000), 164(3), 1148-1152). Thus, the NK1.1$^+$, CD8$^+$ cells are also highly likely to show a cytotoxic activity, and these cells are assumed to be deeply involved in the occurrence of GVHD. In the G-CSF-treated recipient mice, GVHD was suppressed, and percent of NK1.1$^+$, CD8$^+$ cells in the peripheral blood mononuclear cells were decreased, dependently on the dose of G-CSF (see Experimental Example 2). Based on these results, it was found that GVHD is suppressed by administering G-CSF to the recipient mice after SPC transplantation. In experiments on peripheral blood stem cell transplantation, splenic stem cells are used in place of peripheral blood stem cells (Blood, Vol. 93, No. 12 (June 15), 1999:p4071-4078). A comparison between peripheral blood stem cell transplantation and splenic stem cell transplantation showed similarities in the phenomenon of increase of stem cells induction in the peripheral blood and splenic cells after administration of G-CSF, the cell surface antigen of stem cells, and the status of occurrence of GVHD in the recipient after cell transfer. Thus, G-CSF treatment is presumed to have the same GVHD suppressing activity in peripheral blood stem cell transplantation as in splenic stem cell transplantation.

PREFERRED MODE FOR CARRYING OUT THE INVENTION

Any highly purified human G-CSF's can be used as the G-CSF that is the active ingredient of the present invention. Concretely, the G-CSF includes those which have substantially the same biological activity as that of mammalian, especially human, G-CSF, and which are naturally occurring ones, ones obtained by the recombinant DNA method, and the chemically modified products of the resulting G-CSF. The G-CSF obtained by the recombinant DNA method includes those having the same amino acid sequence as that of natural G-CSF, or those in which one or more amino acids of the amino acid sequence have been deleted or substituted, or in which one or more amino acids have been added to the amino acid sequence, and which have the above-mentioned biological activity.

G-CSF in the present invention may be produced by any method, and includes those produced by culture cell lines of human tumor cells, extracting, separating and purifying G-CSF by various methods, or those obtained by gene engineered *Escherichia coli,* yeast, Chinese hamster ovary (CHO) cells, C127 cells, etc. to produce G-CSF, extracting, separating and purifying the G-CSF by various methods. The most preferred G-CSF is that produced by CHO cells by use of recombinant DNA technology (for example, including those described in Japanese Patent Publication No. 1989-44200, Japanese Patent Publication No. 1990-5395, Japanese Unexamined Patent Publication No. 1987-129298, Japanese Unexamined Patent Publication No. 1987-132899, Japanese Unexamined Patent Publication No. 1987-236488, and Japanese Unexamined Patent Publication No. 1989-85098).

Further, the GVHD suppressant of the present invention may, if desired, have a suspending agent, a solution adjuvant, a stabilizer, a tonicity agent, a preservative, and an adsorption preventive, etc. added thereto according to the method of administration or the dosage form. Examples of the suspending agent include methylcellulose, polysorbate 80, hydroxyethylcellulose, acacia, tragacanth powder, sodium carboxymethylcellulose, and polyoxyethylene sorbitan monolaurate. Examples of the solution adjuvant include polyoxyethylene hydrogenated castor oil, polysorbate 80, nicotinamide, polyoxyethylene sorbitan monolaurate, macrogol, and ethyl castor oil fatty acid. Examples of the stabilizer include human serum albumin, dextran 40, methylcellulose, gelatin, sodium sulfite, and sodium metasulfite. Examples of the tonicity agent include D-mannitol and sorbitol. Examples of the preservative include methyl parahyroxybenzoate, ethyl parahydroxybenzoate, sorbic acid, phenol, cresol, and chlorocresol. Examples of the adsorption preventive include human serum albumin, lecithin, dextran, ethylene oxide-propylene oxide copolymer, hydroxypropylcellulose, methylcellulose, polyoxyethylene hydrogenated castor oil, and polyethylene glycol.

The pharmaceutical composition containing human G-CSF as an active ingredient, according to the present invention, may be in the form of an injection (subcutaneous, intradermal, intramuscular, intravenous and intraperitoneal), or in a dosage form suitable for percutaneous, transmucosal or transnasal administration, or in a dosage form suitable for oral administration (tablets, capsules, granules, liquids and solutions, suspensions).

The pharmaceutical composition of the present invention containing human G-CSF as an active ingredient is effective in suppressing acute GVHD and chronic GVHD. The pharmaceutical composition of the present invention is also considered to be effective for the suppression of not only GVHD after peripheral blood stem cell transplantation, but also GVHD after other hematopoietic stem cell transplantation excluding bone marrow cell transplantation.

The dose of G-CSF contained in a preparation having the G-CSF as an active ingredient, and the frequency of injection with the preparation can be determined in consideration of the disease status of a patient with a target disease. Normally, a preparation containing human G-CSF in a dose of 0.1 μg/kg to 100 μg/kg, preferably 1 μg/kg to 10 μg/kg, per adult can be administered once daily, twice daily, i.e., in the morning and in the evening, or three times daily, i.e., in the morning, at noon, and in the evening. However, the present invention is not restricted by the content, administration route, the frequency of injection, etc. of human G-CSF. If G-CSF is administered in an attempt to promote the increase of the neutrophil count at the time of hematopoietic stem cell transplantation, G-CSF treatment needs to be discontinued when the neutrophil count has increased to a certain extent (e.g., to a neutrophil count of 5,000/mm$^3$ or more). If G-CSF is administered for the purpose of suppressing GVHD, G-CSF treatment can be continued in order to suppress GVHD, even when the neutrophil count has increased to a certain extent. The onset of treatment with G-CSF is not restricted, either.

The present invention will be described in further detail by the following Experimental Examples and Examples:

<Experimental Example 1>

Experiments on Survival-Prolonging Effect

G-CSF (CHUGAI PHARMACEUTICAL), 100 μg/kg, was subcutaneously administered to 6- to 10-week-old male C57BL/6N donor mice (Nippon Charlesriver) twice daily, in the morning (8:00-10:00) and in the evening (16:00-18:00), for 4 days, and in the morning on the 5th day to induce stem cells in the spleen. The splenic cells (2.5×10$^7$ cells/head) of the donor mice were transferred into 6- to 10-week-old female BALB/c recipient mice (Nippon Charlesriver)

through the tail vein, the recipient mice having been irradiated with a lethal dose of irradiation (X-rays; 850 R). G-CSF, 10, 30 or 100 µg/kg, was subcutaneously administered to the recipient mice for 7 days, starting on the day following the splenic cell transfer. Then, a schedule including drug withdrawal for 2 days and drug treatment for 5 days was repeated during the study period. A control group received a diluent for G-CSF (vehicle: 0.01% Tween 20 (Nikko Chemical), 5% mannitol (Nakaraitesk) solution). The occurrence of GVHD in the recipient mice was evaluated on the survival rate and changes in the body weight. The results on the survival rate are shown in FIG. 1. As the results show, the average number of days of survival in the recipient mice of the control group (Vehicle group) was 17.0±2.71 days. On the other hand, the average number of days of survival in the recipient mice of the G-CSF treatment group was 24.3±1.05 days ($p<0.05$) in the 10 µg/kg group, 37.4±3.91 days ($p<0.005$) in the 30 µg/kg group, and 33.0±1.15 days ($p<0.001$) in the 100 µg/kg group, indicating significant survival-prolonging effects in comparison with the control group. This survival-prolonging effect was the most potent in the group receiving 30 µg/kg G-CSF. A weight decrease, an indicator of GVHD occurrence, was observed in dead mice. Thus, the cause of death in these mice was assumed to be GVHD. The survival-prolonging effect by subcutaneous administration of G-CSF, demonstrated in the present study, is considered to have resulted from the suppression of GVHD occurrence.

<Experimental Example 2>

Experiments on Suppression of Cell Proliferation

Figure 2:
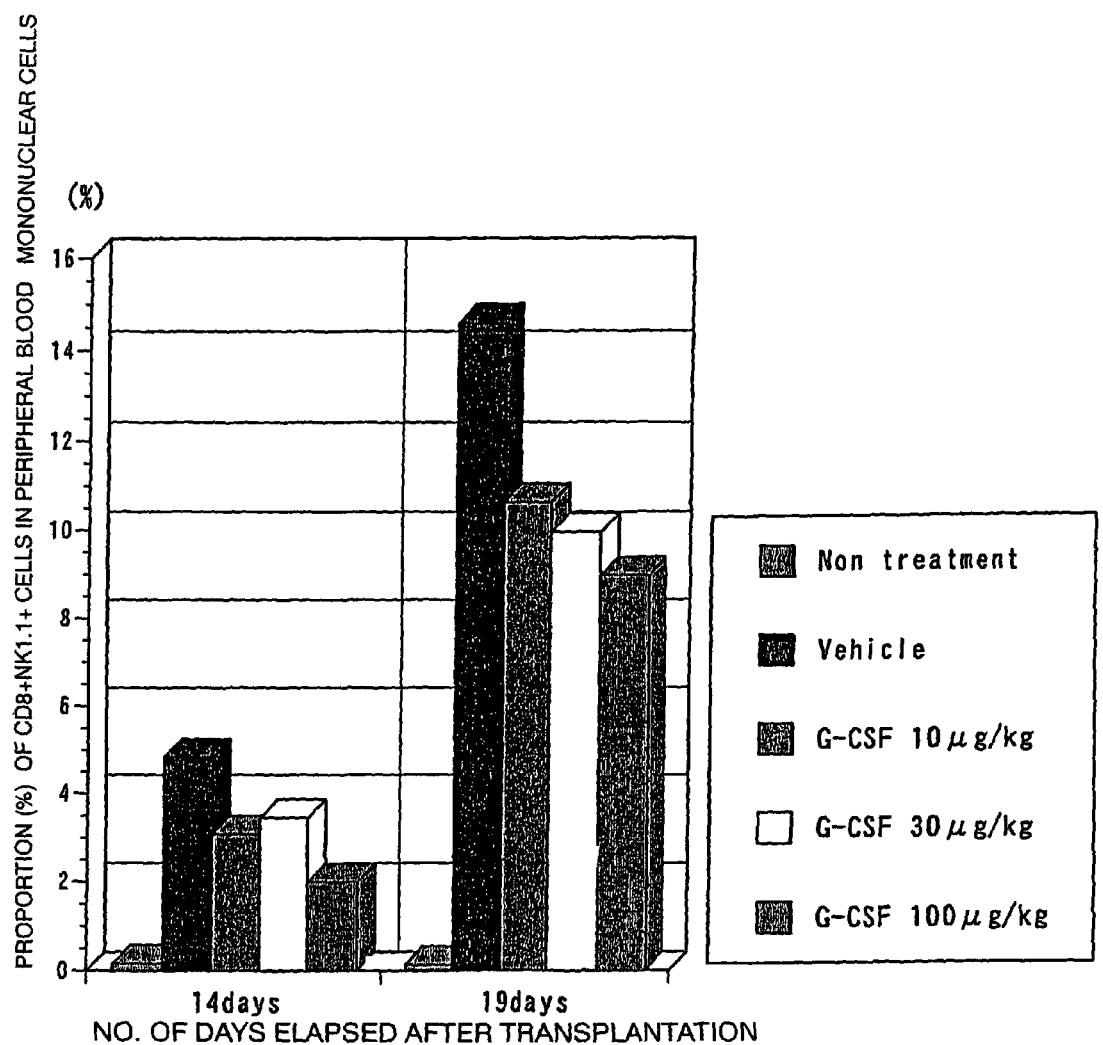
FIG. 2 is a graph showing the effect of G-CSF administration on the proportion of NK1.1-positive CD8-positive cells in peripheral blood mononuclear cells after splenic cell transplantation into recipient mice. The vertical axis of the graph shows the proportion (%) of NK1.1-positive CD8-positive cells in peripheral blood. The horizontal axis shows the days mononuclear cells after transplantation.

To identify a cell population involved in GVHD, cell populations in the peripheral blood mononuclear cells of the recipient mice on the 19th day of cell transfer, which were used in Experiment 1, were investigated by flow cytometry (FACScan: Becton Dickinson). The peripheral blood (about 20 µL) was collected from the dorsal metatarsal veins of the mice in each group, and stained with PE-labeled anti-CD8 antibody, or FITC-labeled anti-NK1.1 antibody (Pharmingen) for 30 minutes at 4° C. Then, each of the stained samples was hemolyzed with 0.75% ammonium chloride Tris-HCl buffer, then washed twice with a culture medium for FACS (20% FCS, 0.1% $NaN_3$, 10 mM PBS), and analyzed for the proportions of the cells with the use of the FACScan. The results are shown in FIG. 2.

The proportion of $NK1.1^+$, $CD8^+$ cells detected in the control group was 14.6%. In the G-CSF treatment group, the proportion of $NK1.1^+$, $CD8^+$ cells were 10.6% in the 10 µg/kg group, 10.0% in the 30 µg/kg group, and 9.0% in the 100 µg/kg group, showing decreases dose-dependent manner. The value in the 100 µg/kg group was about a half of that in the control group. The $NK1.1^+$, $CD8^+$ cells were not observed in the normal mice (BALB/c, C57BL/6N), and not observed when syngeneic C57BL/6N mice were used as the recipient mice. Furthermore, the proportion of the $NK1.1^+$, $CD8^+$ cells was found to be closely reversely correlated with the survival rate of the mice. These results suggested that the $NK1.1^+$, $CD8^+$ cells play a central role in the occurrence of GVHD. Hence, the in vivo administration of G-CSF is thought to have suppressed the induction of $NK1.1^+$, $CD8^+$ cells with cytotoxic activity, and have inhibited the occurrence of GVHD.

<Example 1>

Preparation Example

Polysorbate 20 (Tween 20: polyoxyethylene sorbitan monolaurate), a nonionic surface active agent, was added in an amount of 0.1 mg/mL to 50 µg/mL of human G-CSF (10 mM phosphate buffer, pH 7.0), and the osmotic pressure was adjusted to 1 with NaCl. Then, the mixture was sterilized by filtration through a membrane filter having a pore size of 0.22 µm. The filtrated solution was charged into a sterilized vial. The vial was sealed with a sterilized rubber stopper and clamped with an aluminum cap to obtain a injection solution. This injection solution is stored at below 10° C. in dark place.

<Example 2>

Preparation Example

Polysorbate 80 (Tween 80: polyoxyethylene sorbitan monooleate), a nonionic surface active agent, was added in an amount of 0.1 mg/mL to 100 µg/mL of human G-CSF (10 mM phosphate buffer, pH 7.0), and the osmotic pressure was adjusted to 1 with NaCl. Then, the mixture was sterilized by filtration through a membrane filter having a pore size of 0.22 µm. The filtrated solution was charged into a sterilized vial. The vial was sealed with a sterilized rubber stopper and clamped with an aluminum cap to obtain a injection solution. This injection solution is stored at below 10° C. in dark place.

<Example 3>

Preparation Example

To 50 µg/ml of human G-CSF (10 mM phosphate buffer, pH 7.0), 0.1 mg/mL of the nonionic surface active agent polysorbate 20 (Tween 20: polyoxyethylene sorbitan monolaurate), 10 mg/mL of HSA and 50 mg/ml of mannitol were added, and dissolved. Then, the solution was sterilized by filtration through a membrane filter having a pore size of 0.22 µm. The solution was charged into a sterilized vial. The vial was loosely sealed with a sterilized rubber stopper and was freeze-dried to obtain a lyophilized preparation for injection. The lyophilized preparation is stored below room temperature, and is dissolved with distilled water for injection just before use.

Field of Industrial Application

The pharmaceutical composition of the present invention containing human G-CSF as an active ingredient is considered to be effective not only for suppressing acute GVHD and chronic GVHD, but also for suppressing GVHD after cord blood stem cell transplantation.

The invention claimed is:
1. A method for suppressing graft-versus-host-disease in a patient transplanted with hematopoietic stem cells consisting of:
   (a) administering hematopoietic stem cells by transplantation to a patient in need thereof; and
   (b) administering to said patient an effective amount of human granulocyte-stimulating factor to suppress graft-versus-host-disease following hematopoietic stem cell transplantation;
   wherein said granulocyte-colony stimulating factor has the same amino acid sequence as a naturally occurring granulocyte-colony stimulating factor, and
   wherein said transplantation excludes bone marrow cell transplantation.

* * * * *